Jan. 19, 1954 G MERRILL Plant Pat. 1,246
PEACH TREE
Filed Feb. 9, 1953
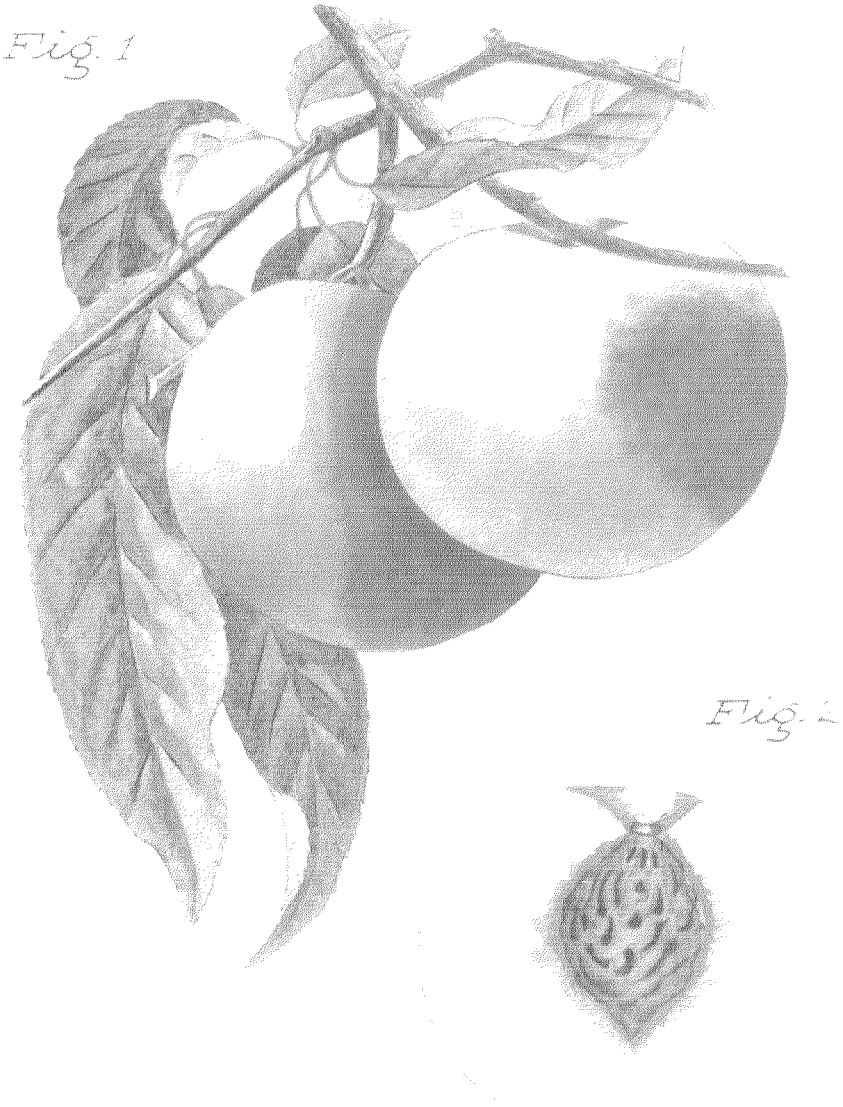
WITNESS
Addison E. Avery
INVENTOR
Grant Merrill
ATTYS.

Patented Jan. 19, 1954

Plant Pat. 1,246

UNITED STATES PATENT OFFICE 1,246

PEACH TREE

Grant Merrill, Red Bluff, Calif.

Application February 9, 1953, Serial No. 336,026

1 Claim. (Cl. 47—62)

The present invention relates to a new and distinct variety of peach tree; such tree bearing large, round, uniform, smooth, yellow fleshed fruit; which fruit is intermediate in type between the July Elberta peach (United States Plant No. 15) and the J. H. Hale peach (unpatented).

The distinguishing characteristics of the instant variety of peach tree are a ripening period of the fruit intermediate the July Elberta peach and the J. H. Hale peach, and fruit which is larger, firmer, and better colored than said July Elberta, but not quite as large or as firm as the J. H. Hale peach.

Additionally, the present variety is characterized by a very large and strong tree; blossoms which are self-fertile; and by being a very heavy producer.

As the fruit of the instant variety is in harvest between the July Elberta peach and the J. H. Hale peach, it is of substantial commercial value, which value is enhanced by the fact that the fruit has excellent shipping and eating qualities.

The herein claimed variety of peach was originated by me in a test plot on my ranch near Red Bluff, county of Tehama, California, as a cross of the J. H. Hale peach (unpatented) and the Currie peach (unpatented).

Subsequent to origination of the present variety, in the manner above described, I have successfully asexually reproduced it by grafting onto root stock in a test plot on my ranch located as aforesaid. These reproductions were found, upon exacting comparison, to carry forward each and every one of the novel characteristics of the parent tree.

In the original drawings:

Fig. 1 is an elevation of one of the fruit of the new and distinct variety, together with twigs and leaves.

Fig. 2 is a sectional elevation of one of the fruit, with the stone exposed but remaining in place.

Referring now more specifically to the pomological details of this new and distinct variety of peach tree, the following is an outline description thereof; all major color plate identifications being by reference to Maerz and Paul Dictionary of Color:

Tree: Very large; very vigorous; upright; open; vasiform; very productive; regular bearer.

Trunk: Medium stockiness; medium shagginess.

Branches: Medium stockiness; medium shagginess.

*Color.*—Gray-brown.

*Lenticels.*—Medium quantity; medium size.

Leaves: Medium size. Length—$6\frac{5}{16}$'' to $7\frac{23}{32}$'', average $7\frac{1}{16}$''; width—$1\frac{5}{8}$'' to $2\frac{1}{32}$'', average $1\frac{27}{32}$''. Shape—lanceolate, acuminate. Medium thickness; smooth.

*Color.*—Top side—medium green (23–L–7). Under side—lighter green (22–K–6).

*Margin.*—Finely crenate.

*Petiole.*—Medium length; medium thickness.

*Glands.*—Two to five, average three. Medium size; alternate spacing. Shape—reniform. Color—red. Position—on petiole and base of leaf.

*Stipules.*—On new growth, dropping off early.

Flower buds: Medium size; medium length. Shape—obtuse. Free; pubescent.

Flowers: Date of first bloom—March 13. Date of full bloom—March 24. Mid-season to late. Medium size. Color—pink to light red.

Fruit: Date of first picking at Red Bluff, California, July 21, 1952. Date of last picking at Red Bluff, California, July 28, 1952.

*Size.*—Large. Average diameter axially—$2\frac{13}{16}$''; average transverse diameter in suture plane—3''; average cheek to cheek diameter—$3\frac{1}{32}$''.

*Form.*—Uniform; symmetrical; globose.

*Suture.*—Distinct; shallow. Continuous from base to apex, but discontinuous from apex over entire circumference. Slight depression beyond pistil point.

*Ventral surface.*—Rounded slightly; tendency toward being lipped on one side. Lipped from base to apex. Lips—unequal tendency.

*Cavity.*—Flaring, elliptical; elongated in suture plane, with suture showing on one side. Markings—yellow, with occasional red streaks extending into cavity. Average depth—$\frac{1}{2}$''; breadth—$\frac{5}{8}$'' to $1\frac{1}{16}$'', average $\frac{27}{32}$''.

*Base.*—Round to slightly oblique.

*Apex.*—Short; mucronate. Pistil point—oblique.

Skin: Medium thick; tough; non-astringent.

*Tendency to crack.*—None in dry weather.

*Color.*—Yellow (9–K–5, shading to 11–K–9), with relatively deep reddish blush 4–L–5, shading to 6–L–6).

*Down.*—Moderate quantity; short length. Rolls up when rubbed.

Flesh:

*Color.*—Yellow (9–L–6, shading to 9–L–8), with red (4–L–5) immediate the stone, somewhat lighter outwardly (1–J–9).

*Surface of pit cavity.*—Pink with pink fibres having cream tips.
*Amygdalin.*—Scant.
*Juice.*—Moderate; rich.
*Texture.*—Firm; fine; melting.
*Fibres.*—Abundant; fine to medium; tender.
*Ripens.*—Evenly.
*Flavor.*—Delicate and mild.
*Aroma.*—Distinct.
*Eating quality.*—Best. Remains firm when skin is fairly well colored.

Stone: Free. Fibres long. Parts from flesh smoothly. Tends to retain some short fibre-like threads along ventral ridge near base.

*Size.* — Medium. Average length — $1\frac{9}{16}''$; average breadth—$1\frac{1}{16}''$; average thickness—$\frac{3}{4}''$.
*Form.*—Ovoid cuneate toward base.
*Base.*—Oblique.
*Hilum.*—Oval.
*Apex.*—Acute.
*Sides.*—Slightly unequal; curved on one side.
*Surface.*—Regularly furrowed near apex toward ventral edge. Pitted from base toward center.
*Ridges.*—Rounded towards apex. On either side, interrupted.
*Pits.*—Elongated.
*Ventral edge.* — Medium thickness, with winged tendency toward base.

*Dorsal edge.*—Medium thickness, with medium groove from base to apex throughout.
*Color.*—Reddish brown (7–E–12). Red when first open, turning to reddish brown upon oxidation.
*Tendency to split.*—Very slight.

Use: Market; dessert; local; Long distance shipment; culinary; canning; freezing.
Keeping quality: Good.
Shipping quality: Excellent.

The tree and its fruit herein described may vary in slight detail due to climatic and soil conditions under which the variety may be grown.

Having thus described the invention, I claim:

A new and distinct variety of peach tree, substantially as described and illustrated, bearing large, round, uniform, smooth, yellow-fleshed fruit; characterized—as to novelty—by a ripening period intermediate the July Elberta peach and the J. H. Hale peach; by a very large, heavy producing tree; by self-fertile blossoms; by fruit larger, firmer, and better colored than the July Elberta, but not as large or as firm as the J. H. Hale; and by fruit which has excellent shipping quality.

GRANT MERRILL.

No references cited.